United States Patent [19]

Johansson

[11] Patent Number: 4,478,570
[45] Date of Patent: Oct. 23, 1984

[54] FLOW CONTROL DEVICE FOR DISPOSABLE GAS LIGHTER

[75] Inventor: Stig Johansson, Jönköping, Sweden

[73] Assignee: Feudor S.A., Venissieux, France

[21] Appl. No.: 298,725

[22] Filed: Sep. 2, 1981

[30] Foreign Application Priority Data

Sep. 5, 1980 [FR] France .................. 80 19585

[51] Int. Cl.³ .............................................. F23D 13/04
[52] U.S. Cl. ................................... 431/344; 431/131
[58] Field of Search ............... 431/130, 131, 142, 143, 431/150, 254, 255, 276, 277, 344; 137/550; 222/3; 251/118, 123

[56] References Cited

U.S. PATENT DOCUMENTS

| 2,732,699 | 1/1956 | Ward | 431/131 |
| 3,597,140 | 8/1971 | Rabe | 431/131 |
| 3,854,862 | 12/1974 | Webster | 431/344 X |
| 3,963,413 | 6/1976 | Lockwood et al. | 431/276 |
| 4,101,262 | 7/1978 | Neyret | 431/344 |
| 4,153,233 | 5/1979 | Neyret | 431/344 X |
| 4,177,646 | 12/1979 | Guadagnin et al. | 431/344 X |
| 4,243,377 | 1/1981 | Schmid | 431/344 |

FOREIGN PATENT DOCUMENTS 1057471 10/1953 France ...................... 431/130

Primary Examiner—Margaret A. Focarino
Attorney, Agent, or Firm—Karl F. Ross; Herbert Dubno

[57] ABSTRACT

A disposable gas lighter of the butane-fuel type comprises a flow-reducing membrane upstream of the valve and designed to limit the height of the flame. The membrane includes a mesoporous layer whose pores have a radius ranging from 20 to 500 Ångstroms and positioned so that an upstream face of this membrane communicates directly with the interior of the liquid fuel reservoir, i.e. without a wicking structure.

7 Claims, 2 Drawing Figures

U.S. Patent        Oct. 23, 1984        4,478,570
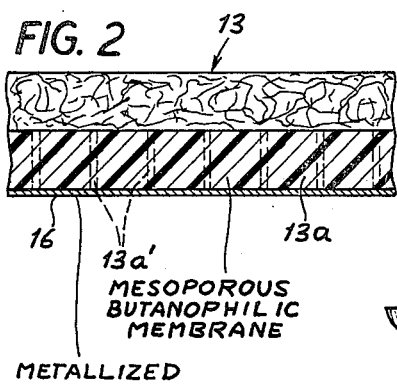
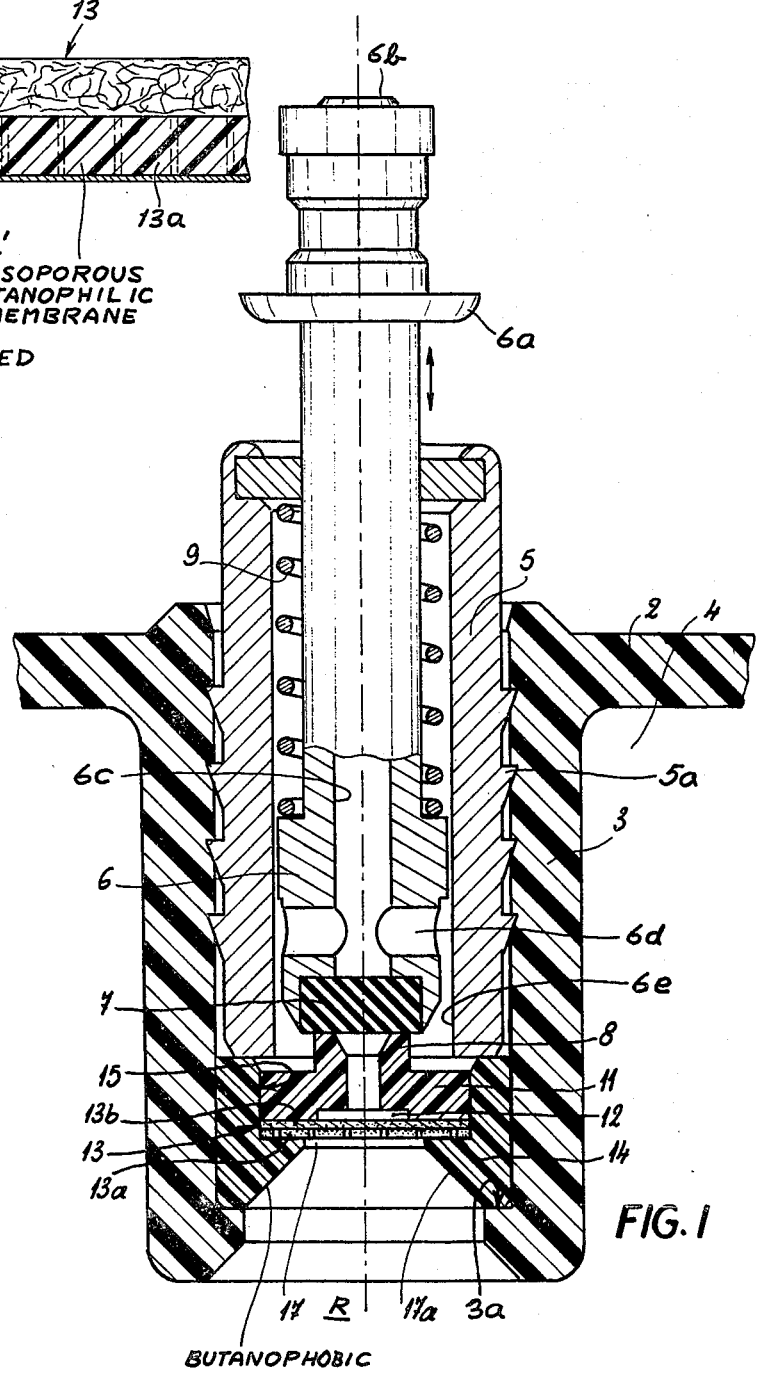

FLOW CONTROL DEVICE FOR DISPOSABLE GAS LIGHTER

FIELD OF THE INVENTION

My present invention relates to a disposable gas lighter and, more particularly, to a butane-fueled gas lighter of the type which comprises a liquid-fuel reservoir and a flow control system at an upper portion of this reservoir including a valve which, when opened, enables a stream of the butane fuel to emerge and to be ignited by a striking mechanism which can be provided at the upper part of the lighter as well. Specifically the invention relates to a flow control system for a lighter of this type.

BACKGROUND OF THE INVENTION

Disposable lighters generally comprise, as noted above, a container for a gasifiable liquid fuel, namely, a hydrocarbon such as butane or mixtures of butane with other hydrocarbons, a valve arrangement at an upper portion of this vessel which can form a nozzle or outlet for a stream of the gasified fuel when the valve is opened, e.g. by manipulation of a lever, and a striking mechanism for generating a spark to ignite this stream of fuel.

A unique flow control system for disposable gas lighters of this type is disclosed in U.S. Pat. Nos. 4,101,262 issued July 18, 1978 and 4,224,020, issued Sept. 23, 1980, and comprises a filter disposed between the valve and the fuel supply, the filter comprising a porous membrane wettable by the hydrocarbon fuel and having porosity characteristics determined at the time of manufacture and establishing the height of the flame.

The advantage of the use of this membrane, which spans the space between the reservoir and the release valve, is that special means for adjusting flame height can be eliminated and/or an excessive flame height can be prevented, thereby restricting the possibility of danger to the user if the flame height has been improperly set by any adjustment mechanism.

Thus the result is a reducing valve system which makes it possible to obtain a constant gas outflow and therefore a constant flame height which is practically independent of the age of the lighter and the ambient temperature.

This arrangement and arrangements which allow adjustability of the flame height are frequently provided with wicking structures leading from the fuel reservoir to the valve system. The wicking structure is designed to draw the liquid fuel into an evaporation chamber in which thermal energy generated by ambient temperature or the flame and transmitted to the evaporation chamber ensures evaporation of the liquid fuel in a uniform manner.

Systems have been developed, e.g. as described in U.S. Pat. No. 4,060,202, granted Nov. 29, 1977, to promote the transfer of heat into the region at which evaporation is to occur.

Another advantage of the provision of means for establishing a fixed flame height in the manner described is that the means for controlling the flame height can be eliminated and the cost of the unit reduced, while avoiding any danger which may result from a malfunction of this control means.

OBJECTS OF THE INVENTION

It is the principal object of the present invention to provide a valve system of the type described, i.e. a valve system with means for fixing the flame height, which is of still more simple construction and design, is of low cost, and is of greater reliability than earlier systems provided for this purpose.

It is another object of the invention to provide an improved disposable gas lighter embodying advantages of the earlier systems described but free from some of the disadvantages thereof.

SUMMARY OF THE INVENTION

I have now discovered, most surprisingly, that when a filter structure is provided upstream of the outlet valve of a disposable lighter of the type described and includes a mesoporous membrane, it is possible to eliminate completely the wicking systems hitherto required and yet obtain reliable delivery of the fuel in a gaseous form at a predetermined rate and thereby fix the flame height, provided the upstream face of this membrane is disposed in direct communication with the interior of the liquid-fuel reservoir.

While the membrane and the filter will be discussed in greater detail below, it should be noted that by a mesoporous membrane I mean a membrane which has pores of a radius ranging from 20 to 500 Ångstrom units.

Thus, according to the present invention, a valve system for a disposable lighter comprises the mechanically actuatable valve capable of sealing off the outflow of the gaseous fuel in one position but capable of being opened to permit a stream of the gasified fuel to emerge and, between this valve and the reservoir containing the liquid hydrocarbon, especially butane, a filter structure which includes the mesoporous membrane as defined having an upstream face directly communicating with the interior of the liquid-fuel reservoir, i.e. in communication with the liquid-fuel reservoir without interposition of any wicking structure.

The invention is based upon my surprising discovery that the flow of fuel through a mesoporous membrane occurs in a condensed state even if upstream of this membrane the fuel is in the gaseous state. This is because a capillary condensation appears to occur due to the decrease in saturation pressure which occurs at a curved interface, i.e. the pores of this membrane. Not only is the wick, therefore, superfluous, but problems in mounting, positioning and installing the wick can be completely eliminated and the system operates effectively regardless of the position in which the lighter is held.

I have found, further, that the support structures for the filter and the membrane can advantageously be composed of a material having low thermal conductivity, e.g. of a plastic or synthetic resin material without any disadvantage to flame stability since it is not essential that thermal energy be delivered to the membrane or filter to assure vaporization of the fuel which appears to volatilize immediately upon passage through the membrane. Thus, while a condensation appears to occur within the membrane as a result of the mesoporous nature thereof, the immediate increase of the saturation pressure downstream of this membrane appears to ensure effective volatilization.

Obviously, the construction of the support for the membrane of synthetic resin material has the further advantage of reducing the cost of the valve system and lighter to an even greater extent.

It has also been found to be advantageous for improved flame stability to form the synthetic-resin or plastic support for the filter so that it has a low wettability with respect to butane, i.e. is butanophobic, while the mesoporous membrane has a high wettability with respect to butane, i.e. is butanophilic.

This has been found to guarantee that fuel located upstream and in contact with the membrane is always in the gaseous state at least when the lighter is held in any normal position for use. The plastic material can be made butanophobic by solvation of the surfaces of this material, e.g. by oxidation with potassium permanganate and concentrated sulfuric acid. The surface tension of the plastic walls of the chamber located upstream of the membrane can thereby be decreased.

According to still another feature of the invention, I can prevent liquid fuel from adhering to the walls of the chamber located upstream of the membrane in normal positions of use of the lighter by making these walls frustoconical or truncated with the small base located on the side toward the membrane, i.e. proximal to the membrane, while the broad base of the frustoconical or frustopyramidal chamber is remote from the membrane.

On occasion it has been discovered that some liquid fuel may be present at the upstream face of the membrane and when this may be the case, it has been found to be advantageous to metalize this upstream face so as to distribute heat uniformly thereover. The upstream face may be formed by or applied to a porous aluminum foil or a metalization layer may be applied by vacuum deposition to this upstream face and, of course, is similarly porous.

BRIEF DESCRIPTION OF THE DRAWING

The above and other objects, features and advantages of the present invention will become more readily apparent from the following description, reference being made to the accompanying drawing in which:

FIG. 1 is a diagrammatic axial section of the valve system for a disposable lighter in accordance with the present invention; and FIG. 2 is a diagrammatic section through a filter provided with a mesoporous membrane of the type used in the valve system of FIG. 1 but drawn to a much larger scale.

SPECIFIC DESCRIPTION

FIG. 1 shows only the part of the head or upper portion of the body 2 of a gas lighter provided the valve system, this body extending downwardly and defining a reservoir R for the liquid fuel which is preferably butane or a mixture of butane with other hydrocarbons.

As shown in FIG. 1, the upper portion of the body 2 of the lighter has a cylindrical well 3 projecting inwardly into the space 4 enclosed by the body 2. The cylindrical well is open axially at each of its ends and receives the force-fitted body 5 of the valve (see U.S. Pat. Nos. 4,101,262 and 4,224,020). More specifically, the metal cylindrical valve body 5 is formed along its outer periphery with annular ribs 5a which, upon axial insertion of this body into the well, penetrate and seize in the synthetic-resin wall of the well.

At its bottom end, the well is provided with an inwardly extending shoulder 3a against which the lower end of member 5 retains a lower support body 14.

Within the tubular body 5 I have fitted an axially displaceable valve member and burner 6 whose upper end is formed with a collar 6a enabling it to be engaged by a lever so that, upon displacement of this lever, the valve member 6 can be raised to release gas through the burner mouth 6b which communicates via an axial bore 6c and radial bores 6d with a space 6e surrounding the lower end of the valve member 6.

At the lower end of this valve member 6, there is provided a sealing disk 7 which is held by a spring 9 against a seat 8 formed as a boss on an upper support member 11.

Thus, when the seal 7 is retracted from the seat, i.e. the valve member 6 is displaced upwardly, gas flows through the seat 8 into the space 6e and thence via passages 6d and 6c through the burner outlet 6b where the gas can be ignited via a piezoelectric or mechanical striker generating a spark in the usual manner.

The support body 11 is provided, at its side opposite the boss 8, with a cavity 12 forming an evaporation chamber and spanned by a reducing valve filter generally represented at 13 and maintained flat against the lower face of body 11 by the support body 14, the upper face of which has a cylindrical recess 15 accommodating part 11.

As is clear from FIG. 1, therefore, the periphery of the filter 13 is clamped between parts 11 and 14.

The filter 13 (FIGS. 1 and 2) consists of a mesoporous membrane 13a, the upper face of which can be covered by a porous sheet 13b. The mesoporous membrane has pores which can have a radius ranging from 20 to 500 Ångstrom units and advantageously is composed of a molecularly oriented polyolefin, especially polypropylene or polyethylene. These materials are inherently butanophilic.

In addition, as is clear from FIG. 1, the lower face of membrane 13a is in direct communication with the interior R of the reservoir through a channel 17 formed in the support body 14.

Thus no wick is required or desired, capillary condensation taking place as gases from the reservoir pass through the mesoporous membrane. Although surprising, it has been noted that such phase transformations occur in the membrane 13a even though this membrane is in an isothermal state and no heat whatsoever is transmitted to the membrane. Consequently constant gas flow can be obtained and the flame is extremely stable, defined by the membrane characteristics as to flame height. Parts 11 and 14 are composed of synthetic resin or plastic material at substantially lower cost then brass or like materials which have been used heretofore.

To ensure that the fuel is in a gaseous state upstream of the mesoporous membrane, the membrane is butanophilic as noted and the support body 14 is treated along the wall of channel 17 to be butanophobic by oxidation with potassium permanganate and concentrated sulfuric acid. The truncated shape of the channel 17 also assists to this end.

Thus even when the lighter has been overturned and liquid fuel fills the channel, when the lighter is returned to its normal upright state the fuel drains rapidly and retention of liquid fuel in the channel is precluded by the butanophobic character of the wall thereof.

As is also apparent from FIG. 2, a metal foil or metalization layer 16 may be applied to the upstream side of the membrane 13a to form a porous heat-distributing lamination or covering which also assists in ensuring that the fuel passing into the membrane will be of a gaseous state. The metal is preferably aluminum.

I claim:

1. In a wickless disposable lighter having a lighter body forming a reservoir for a liquid hydrocarbon fuel and a valve system mounted in said body, the combination wherein said valve system comprises a valve for selectively releasing a stream of fuel from said body, a support disposed upstream of said valve and between said valve and said reservoir, and a maximum-flame-height-reducing valve member mounted in said support and disposed between said valve and said reservoir, said member comprising a mesoporous membrane having a high wettability with respect to the hydrocarbon fuel and pores of a radius ranging from 20 to 500 Ångstrom units with an upstream side of said membrane directly in communication with said liquid reservoir.

2. The improvement defined in claim 1 wherein said member comprises a porous sheet formed on its upstream side with said membrane.

3. The improvement defined in claim 2 wherein said support is composed of a synthetic resin material of low thermal conductivity.

4. In a wickless disposable lighter having a lighter body forming a reservoir for a liquid hydrocarbon fuel and a valve system mounted in said body, the combination wherein said valve system comprises a valve for selectively releasing a stream of fuel from said body, a support disposed upstream of said valve and between said valve and said reservor, and a maximum-flame-height-reducing valve member mounted in said support and disposed between said valve and said reservoir, said member comprising a mesoporous membrane having a high wettability with respect to the hydrocarbon fuel and pores of a radius ranging from 20 to 500 ngstrom units with an upstream side of said membrane directly in communication with said liquid reservoir, said member comprising a porous sheet formed on is upstream side with said membrane, said support being composed of a synthetic resin material of low thermal conductivity, and being formed with a passage communicating between the upstream side of said membrane and said reservoir, said passage having a butanophobic wall and said membrane being composed of a butanophilic synthetic resin material.

5. The improvement defined in claim 4 wherein said wall is oxidized by treatment with potassium permanganate and concentrated sulfuric acid solution.

6. The improvement defined in claim 4 wherein said passage is of truncated shape having a small base proximal to the upstream side of said membrane.

7. In a wickless disposable lighter having a lighter body forming a reservoir for a liquid hydrocarbon fuel and a valve system mounted in said body, the combination wherein said valve system comprises a valve for selectively releasing a stream of fuel from said body, a support disposed upstream of said valve and between said valve and said reservoir, and a maximum-flame-height-reducing valve member mounted in said support and disposed between said valve and said reservoir, said member comprising a mesoporous membrane having a high wettability with respect to the hydrocarbon fuel and pores of a radius ranging from 20 to 500 ngstrom units with an upstream side of said membrane directly in communication with said liquid reservoir, the upstream side of said membrane being formed with a metallic layer coating the membrane.

* * * * *